US011111193B2

(12) United States Patent
Schoonebeek et al.

(10) Patent No.: US 11,111,193 B2
(45) Date of Patent: *Sep. 7, 2021

(54) TREATMENT OF A MIXED METAL OXIDE CATALYST CONTAINING MOLYBDENUM, VANADIUM, NIOBIUM AND OPTIONALLY TELLURIUM

(71) Applicant: SHELL OIL COMPANY, Houston, TX (US)

(72) Inventors: Ronald Jan Schoonebeek, Amsterdam (NL); Michael Johannes Franciscus Maria Verhaak, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/322,486

(22) PCT Filed: Jun. 29, 2015

(86) PCT No.: PCT/EP2015/064639
§ 371 (c)(1),
(2) Date: Dec. 28, 2016

(87) PCT Pub. No.: WO2016/001112
PCT Pub. Date: Jan. 7, 2016

(65) Prior Publication Data
US 2017/0136447 A1 May 18, 2017

(30) Foreign Application Priority Data

Jun. 30, 2014 (EP) ..................... 14174922

(51) Int. Cl.
C07C 5/48 (2006.01)
B01J 38/04 (2006.01)
C07C 51/16 (2006.01)
B01J 23/28 (2006.01)
B01J 27/30 (2006.01)
B01J 37/08 (2006.01)
B01J 38/14 (2006.01)
B01J 23/92 (2006.01)
B01J 23/00 (2006.01)
B01J 27/057 (2006.01)

(52) U.S. Cl.
CPC ............ C07C 5/48 (2013.01); B01J 23/002 (2013.01); B01J 23/28 (2013.01); B01J 23/92 (2013.01); B01J 27/0576 (2013.01); B01J 27/30 (2013.01); B01J 37/08 (2013.01); B01J 38/04 (2013.01); B01J 38/14 (2013.01); C07C 51/16 (2013.01); B01J 2523/00 (2013.01); C07C 2523/20 (2013.01); C07C 2523/22 (2013.01); C07C 2523/28 (2013.01); C07C 2527/057 (2013.01); Y02P 20/52 (2015.11); Y02P 20/584 (2015.11)

(58) Field of Classification Search
CPC ....................................................... C07C 5/48
See application file for complete search history.

(56) References Cited

U.S. PATENT DOCUMENTS

| 4,899,003 | A | 2/1990 | Manyik et al. |
| 6,143,928 | A | 11/2000 | Karim et al. |
| 6,333,444 | B1 | 12/2001 | Ellis et al. |
| 7,091,377 | B2 | 8/2006 | Borgmeier et al. |
| 7,319,179 | B2 | 1/2008 | Nieto et al. |
| 8,105,972 | B2 | 1/2012 | Gaffney et al. |
| 8,519,210 | B2 † | 8/2013 | Arnold |
| 2003/0158440 | A1 † | 8/2003 | Zeyss |
| 2004/0063989 | A1 | 4/2004 | Hechler et al. |
| 2004/0147393 | A1 | 7/2004 | Hibst et al. |
| 2005/0137422 | A1 | 6/2005 | Hazin et al. |
| 2005/0203312 | A1 | 9/2005 | Cavalcanti et al. |
| 2007/0249740 | A1* | 10/2007 | Iaccino ............ C07C 2/76 518/726 |
| 2007/0249879 | A1* | 10/2007 | Iaccino ............ C07C 2/78 585/418 |
| 2008/0269536 | A1 | 10/2008 | Crone et al. |
| 2009/0287019 | A1 † | 11/2009 | Hazin |
| 2010/0255986 | A1 | 10/2010 | Gaffney et al. |
| 2010/0256432 | A1 | 10/2010 | Arnold et al. |
| 2011/0245571 | A1* | 10/2011 | Kustov ............ C07C 5/48 585/658 |

(Continued)

FOREIGN PATENT DOCUMENTS

CN 1701054 A 11/2005
CN 1703387 A 11/2005

(Continued)

OTHER PUBLICATIONS

International Search Report dated Jul. 23, 2015 of PCT/EP2015/064639 filed Jun. 29, 2015.
Cavani et al., Oxidative Dehydrogenation of Ethane and Propane: How far from Commercial Implementation?, Catalysis Today, vol. 127, Issue No. 1-4, Jul. 2, 2007, pp. 113-131.
International Search Report and Written Opinion Received for PCT Application No. PCT/EP2015/064640, dated Jul. 24, 2015, 10 pages.
International Search Report and Written Opinion Received for PCT Application No. PCT/EP2015/064638, dated Aug. 12, 2015, 10 pages.

(Continued)

Primary Examiner — Philip Y Louie
Assistant Examiner — Alyssa L Cepluch
(74) Attorney, Agent, or Firm — Shell Oil Company

(57) ABSTRACT

The invention relates to a process for treatment of a mixed metal oxide catalyst containing molybdenum, vanadium, niobium and optionally tellurium, comprising contacting a gas stream comprising methane, an inert gas or oxygen or any combination of two or more of these with the catalyst, wherein said gas stream comprises 0 to 25 vol. % of an alkane containing 2 to 6 carbon atoms and/or alkene containing 2 to 6 carbon atoms.

4 Claims, No Drawings

(56) References Cited

U.S. PATENT DOCUMENTS

| | | |
|---|---|---|
| 2013/0072737 A1 | 3/2013 | Kustov et al. |
| 2014/0114109 A1* | 4/2014 | Sanchez Valente ..... B01J 37/08 |
| | | 585/658 |
| 2014/0163290 A1* | 6/2014 | Grune .................... B01J 23/882 |
| | | 585/626 |
| 2014/0275685 A1 | 9/2014 | Valente |
| 2016/0207035 A1 | 7/2016 | Zander et al. |
| 2017/0252728 A1 | 9/2017 | Rooij et al. |

FOREIGN PATENT DOCUMENTS

| | | |
|---|---|---|
| CN | 1705638 A | 12/2005 |
| WO | 2003064035 | 8/2003 |
| WO | 2010096909 | 9/2010 |
| WO | 2013164418 A1 | 11/2013 |

OTHER PUBLICATIONS

Botella et al., "Selective Oxidative Dehydrogenation of Ethane on Movtenbo Mixed Metal Oxide Catalysts", Journal of Catalysis, Academic Press, vol. 225, Issue No. 2, Jul. 25, 2004, pp. 428-438, XP004519142.

Ivars et al., "Selective Oxidation of Short-chain Alkanes Over Hydrothermally Prepared Movtenbo Catalysts", Topics in Catalysis, vol. 38, Issue No. 1-3, Jul. 1, 2006, pp. 59-67, XP019409505.

\* cited by examiner
† cited by third party

TREATMENT OF A MIXED METAL OXIDE CATALYST CONTAINING MOLYBDENUM, VANADIUM, NIOBIUM AND OPTIONALLY TELLURIUM

Priority Claim

The present application is the National Stage (§ 371) of International Application No. PCT/EP2015/064639, filed Jun. 29, 2015, which claims priority from European Patent Application No. 14174922.6, filed Jun. 30, 2014 which is incorporated herein by reference.

FIELD OF THE INVENTION

The present invention relates to a process for treatment of a mixed metal oxide catalyst containing molybdenum (Mo), vanadium (V), niobium (Nb) and optionally tellurium (Te).

BACKGROUND OF THE INVENTION

Mixed metal oxide catalysts containing molybdenum, vanadium, niobium and optionally tellurium may be used in a variety of chemical processes. For example, such catalyst may be used to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum, vanadium, niobium and optionally tellurium as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

Usually, in the course of time, the performance of such catalyst containing Mo, V, Nb and optionally Te, including its activity and/or selectivity, may get reduced by using it. Catalyst performance may be kept at an acceptable level by for example increasing the reaction temperature. However, a disadvantage of such temperature increase is that undesired side-reactions may occur. Therefore, generally, it is desired to treat or regenerate such relatively expensive, used catalyst such that its original performance, including its activity and/or selectivity, is restored or that the performance of the used catalyst is increased to a higher level.

Apart from treating or regenerating used catalysts containing Mo, V, Nb and optionally Te, as discussed above, it is also desired to provide a process for treating fresh catalysts containing Mo, V, Nb and optionally Te, which have not been used as a catalyst in a chemical process before, such as to improve its performance, including its activity and/or selectivity.

Therefore, it is an objective of the present invention to provide a process for treatment of a mixed metal oxide catalyst containing molybdenum, vanadium, niobium and optionally tellurium, which catalyst may be a fresh or used catalyst, which treatment process results in an improvement in catalyst performance, in particular an improvement of the activity and/or selectivity of the catalyst, in particular an improvement of the activity and/or selectivity in an alkane ODH and/or alkene oxidation process wherein such catalyst may be used.

SUMMARY OF THE INVENTION

Surprisingly it was found that such process for treatment of a mixed metal oxide catalyst containing molybdenum, vanadium, niobium and optionally tellurium may be a process which comprises contacting a gas stream comprising methane, an inert gas or oxygen or any combination of two or more of these with the catalyst, wherein said gas stream comprises 0 to 25 vol. % of an alkane containing 2 to 6 carbon atoms and/or alkene containing 2 to 6 carbon atoms, in which case the catalyst performance, including activity and/or selectivity of the catalyst, may be improved.

Accordingly, the present invention relates to a process for treatment of a mixed metal oxide catalyst containing molybdenum, vanadium, niobium and optionally tellurium, comprising contacting a gas stream comprising methane, an inert gas or oxygen or any combination of two or more of these with the catalyst, wherein said gas stream comprises 0 to 25 vol. % of an alkane containing 2 to 6 carbon atoms and/or alkene containing 2 to 6 carbon atoms.

DETAILED DESCRIPTION OF THE INVENTION

While the process of the present invention and the gas stream or gas streams used in said process are described in terms of "comprising", "containing" or "including" one or more various described steps and components, respectively, they can also "consist essentially of" or "consist of" said one or more various described steps and components, respectively.

In the present invention, a mixed metal oxide catalyst containing molybdenum, vanadium, niobium and optionally tellurium is contacted with a gas stream comprising methane, an inert gas or oxygen or any combination of two or more of these. Within the present specification, said gas stream comprising methane, an inert gas or oxygen or any combination of two or more of these is also referred to as "treatment gas stream".

In the present invention, the treatment gas stream comprises 0 to 25 vol. % of an alkane containing 2 to 6 carbon atoms and/or alkene containing 2 to 6 carbon atoms.

Preferably, the treatment gas stream comprises no or substantially no alkane containing 2 to 6 carbon atoms and/or alkene containing 2 to 6 carbon atoms.

Within the present specification, by "substantially no" in relation to the amount of a specific component in a gas stream, it is meant an amount which is at most 10,000, preferably at most 5,000, more preferably at most 1,000, more preferably at most 500, more preferably at most 100, more preferably at most 50, more preferably at most 30, more preferably at most 20, and most preferably at most 10 ppmv (parts per million by volume) of the component in question, based on the amount (i.e. volume) of said gas stream.

In a case wherein in the present process the treatment gas stream also comprises an alkane containing 2 to 6 carbon atoms and/or alkene containing 2 to 6 carbon atoms, the amount of said alkane and/or alkene containing 2 to 6 carbon atoms may be 1 to 25 vol. % or 1 to 10 vol. % or 1 to 5 vol. %.

As mentioned above, the treatment gas stream may comprise an inert gas. Said inert gas may be selected from the group consisting of the noble gases and nitrogen ($N_2$). Preferably, the inert gas is nitrogen or argon, more preferably nitrogen.

Further, in case the treatment gas stream comprises a combination of methane and an inert gas, the volume ratio of methane to inert gas may vary within broad ranges and may be of from 100:1 to 1:100, more suitably 20:1 to 1:20, most suitably 10:1 to 1:10.

Still further, in case the treatment gas stream comprises no combination of methane and an inert gas, the treatment gas stream either comprises methane and no or substantially no inert gas or comprises an inert gas and no or substantially no methane.

In the present process, the treatment gas stream may comprise an amount of methane of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %; an amount of an inert gas of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %; and an amount of oxygen of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %.

Further, in the present process, the treatment gas stream may comprise methane in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

Further, in the present process, the treatment gas stream may comprise an inert gas in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

Further, in the present process, the treatment gas stream may comprise oxygen in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

For example, in the present process, the treatment gas stream may be a gas stream consisting of oxygen, which means that it contains no or substantially no methane and no or substantially no inert gas, preferably no or substantially no component other than oxygen.

However, preferably, in one embodiment of the present process, the treatment gas stream comprises methane and/or an inert gas and no or substantially no oxygen, which embodiment is herein referred to as "Embodiment A". That is to say, in Embodiment A, the treatment gas stream comprises methane, an inert gas or a combination of methane and an inert gas, but the treatment gas stream comprises no or substantially no oxygen.

In said Embodiment A of the present process, the treatment gas stream may comprise methane and/or an inert gas in an amount of from 60 to 100 vol. %, more suitably 75 to 100 vol. %, more suitably 90 to 100 vol. %, more suitably 95 to 100 vol. %, most suitably 99 to 100 vol. %. Further, in said Embodiment A, the treatment gas stream may be a gas stream consisting of methane and/or an inert gas, which means that it contains no or substantially no oxygen, in particular no or substantially no component other than methane and/or inert gas.

Further, preferably, in another embodiment of the present process, the treatment gas stream comprises oxygen and methane and/or an inert gas, which embodiment is herein referred to as "Embodiment B". That is to say, in Embodiment B, the treatment gas stream comprises oxygen and in addition the treatment gas stream also comprises methane, an inert gas or a combination of methane and an inert gas.

In said Embodiment B of the present process, the treatment gas stream may comprise 5 to 35 vol. % of oxygen, more suitably 15 to 30 vol. % of oxygen, and in addition the treatment gas stream may comprise 65 to 95 vol. % of methane and/or an inert gas, more suitably 70 to 85 vol. % of methane and/or an inert gas. Further, in case in said Embodiment B the treatment gas stream additionally comprises methane, ranges for the molar ratio of oxygen to methane in said gas stream which are suitable, are of from 0.01 to 1, more suitably 0.05 to 0.5. Still further, in case in said Embodiment B the treatment gas stream additionally comprises an inert gas, such as nitrogen, the treatment gas stream may be an air stream, optionally diluted with an inert gas, such as nitrogen.

Further, the present process may comprise one step or multiple steps. Still further, said one step or at least one of said multiple steps may comprise contacting a gas stream, as described in any one of the above-mentioned embodiments for the treatment gas stream, with the mixed metal oxide catalyst containing molybdenum, vanadium, niobium and optionally tellurium.

For example, the present process may comprise the following two steps: a first step comprising contacting a gas stream as described in above-mentioned Embodiment B for the treatment gas stream, which gas stream comprises oxygen and methane and/or an inert gas, with the catalyst, followed by a second step comprising contacting a gas stream as described in above-mentioned Embodiment A for the treatment gas stream, which gas stream comprises methane and/or an inert gas and no or substantially no oxygen, with the catalyst.

Preferably, in the present process, the temperature is of from 200 to 500° C. More preferably, said temperature is of from 250 to 500° C., most preferably of from 300 to 500° C.

Preferably, said temperature is at least 200° C., more preferably at least 230° C., more preferably at least 250° C., more preferably at least 270° C., more preferably at least 290° C., more preferably at least 300° C., most preferably at least 320° C.

Further, preferably, said temperature is at most 500° C., more preferably at most 470° C., more preferably at most 450° C., more preferably at most 420° C., more preferably at most 400° C., more preferably at most 380° C., most preferably at most 350° C.

Still further, in the present process, typical pressures are 0.1-20 bara (i.e. "bar absolute"). Further, in a preferred embodiment, said pressure is of from 0.1 to 15 bara, more preferably of from 0.5 to 10 bara, most preferably of from 1 to 5 bara.

The time period for contacting the treatment gas stream with the catalyst may vary within wide ranges and may be of from 10 minutes to 10 hours, more suitably of from 30 minutes to 5 hours.

As mentioned above, the treatment of the present process may be applied to a fresh or used catalyst containing molybdenum, vanadium, niobium and optionally tellurium.

In one embodiment of the present invention, the catalyst is a fresh catalyst. Within the present specification, a "fresh catalyst" means a catalyst which has not been used as a catalyst in a chemical process before. The fresh catalyst is, however, suitable to be used as a catalyst in a chemical process, which means that it is a final catalyst obtained as the product in a catalyst preparation process, and not any intermediate catalyst or catalyst precursor. The present treatment process may be applied in order to improve catalyst performance, including activity and/or selectivity, of such fresh catalyst. Preferably, said fresh catalyst is intended to be used in the oxidative dehydrogenation of an alkane containing 2 to 6 carbon atoms and/or the oxidation of an alkene containing 2 to 6 carbon atoms.

In another embodiment of the present invention, said catalyst is a used catalyst. Within the present specification, a "used catalyst" means a catalyst which has been used as a catalyst in a chemical process. The catalyst performance, including its activity and/or selectivity, may have been decreased through such use. The present treatment process may be applied in order to restore the original catalyst performance, including activity and/or selectivity, of the used catalyst or to increase the performance of the used catalyst to a higher level. Preferably, said used catalyst has been used in the oxidative dehydrogenation of an alkane containing 2 to 6 carbon atoms and/or the oxidation of an alkene containing 2 to 6 carbon atoms.

Preferably, in the present invention, the mixed metal oxide catalyst containing molybdenum, vanadium, niobium and optionally tellurium is a heterogeneous catalyst.

In the present invention, the catalyst is a mixed metal oxide catalyst containing molybdenum, vanadium, niobium and optionally tellurium as the metals, which catalyst may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

As discussed above, the fresh catalyst may be intended to be used as a catalyst in the oxidative dehydrogenation of an alkane containing 2 to 6 carbon atoms and/or the oxidation of an alkene containing 2 to 6 carbon atoms, and the used catalyst may have been used as a catalyst in such chemical process. Preferably, in said alkane oxidative dehydrogenation process, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane. Further, preferably, in said alkene oxidation process, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

The invention is further illustrated by the following Examples.

EXAMPLES (A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen ($N_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material, having a size of 40-80 mesh and composed of porous catalyst particles, was then used in the ethane oxidative dehydrogenation experiments described below.

(B) Catalytic Oxidative Dehydrogenation of Ethane and Subsequent Treatment

In this experiment, the catalyst thus prepared was used in an experiment involving ethane oxidative dehydrogenation (ethane ODH) within a small-scale testing unit comprising a vertically oriented, cylindrical, quartz reactor having an inner diameter of 3.0 mm. 0.65 g of the catalyst was loaded in the reactor. The catalyst bed height was 6 cm. On top of the catalyst bed, another bed having a height of 8 cm was placed which latter bed contained inert silicon carbide (SiC) particles having an average diameter of 0.8 mm.

In this experiment, a gas stream comprising 63 vol. % of ethane, 21 vol. % of oxygen ($O_2$) and 16 vol. % of nitrogen ($N_2$) was fed to the top of the reactor and then sent downwardly through the catalyst bed to the bottom of the reactor. Said gas stream was a combined gas stream comprising a flow of ethane having a rate of 3.00 Nl/hr, a flow of oxygen having a rate of 1.00 Nl/hr and a flow of nitrogen having a rate of 0.77 Nl/hr. "Nl" stands for "normal litre" as measured at standard temperature and pressure, namely 32° F. (0° C.) and 1 bara (100 kPa). The pressure in the reactor was 2.5 bara. The reactor was heated such that the temperature of the catalyst (at the top of the catalyst bed) was 390° C. This condition was maintained for 8 hours. This time period of 8 hours is herein referred to as "reaction period A". Directly after reaction period A, the following sequence of steps was performed:

1. The flow of ethane was gradually stopped and at the same time gradually replaced by a flow of methane having a rate of 3.00 Nl/hr, within a period of time of 3 minutes.
2. The thus obtained condition, comprising a flow of methane having a rate of 3.00 Nl/hr, a flow of oxygen having a rate of 1.00 Nl/hr and a flow of nitrogen having a rate of 0.77 Nl/hr, was maintained for 2 hours. The temperature of the catalyst decreased from 390° C. to 380° C.
3. The flow of oxygen was gradually stopped, within a period of time of 1 minute.
4. The thus obtained condition, comprising a flow of methane having a rate of 3.00 Nl/hr and a flow of nitrogen having a rate of 0.77 Nl/hr, was maintained for 1 hour.
5. A flow of oxygen having a rate of 1.00 Nl/hr was gradually introduced, within a period of time of 1 minute.
6. A flow of ethane having a rate of 3.00 Nl/hr was gradually introduced and at the same time the flow of methane was gradually stopped, within a period of time of 3 minutes.
7. The thus obtained condition, comprising a flow of ethane having a rate of 3.00 Nl/hr, a flow of oxygen having a rate of 1.00 Nl/hr and a flow of nitrogen having a rate of 0.77 Nl/hr, was maintained for 8 hours. This time period of 8 hours is herein referred to as "reaction period B".

The conversion of ethane and the product composition were measured with a gas chromatograph (GC) equipped with a thermal conductivity detector (TCD) and with another GC equipped with a flame ionization detector. Acetic acid by-product and water from the reaction were trapped in a quench pot.

In Table 1 below, the experimental results (conversion of ethane and selectivity towards ethylene) are shown.

TABLE 1

| Time | Conversion of ethane (%) | Selectivity to ethylene (%) |
| --- | --- | --- |
| 4 hours after start of reaction period A (untreated catalyst; comparative) | 44 | 94 |
| 4 hours after start of reaction period B (treated catalyst; invention) | 47 | 93 |

Surprisingly, it appears from Table 1 that by a treatment in accordance with the present invention, of a mixed metal oxide catalyst containing molybdenum, vanadium, niobium and optionally tellurium, that had been used before in a chemical process (in these examples an ethane ODH process), the conversion was increased (see treated catalyst in Table 1) as compared to a case wherein such treatment was not carried out (see untreated catalyst in Table 1). Compare the increased conversion of 47% for the treated catalyst with the conversion of 44% for the untreated catalyst.

That which is claimed is:

1. A process for treatment of a used mixed metal oxide catalyst, the process comprising:
   oxidative dehydrogenation of a feed comprising an alkane containing 2 to 6 carbon atoms and/or oxidation of a feed containing an alkene containing 2 to 6 carbon atoms comprising contacting the feed containing the alkane and/or alkene with a mixed metal oxide catalyst comprising molybdenum, vanadium, niobium, and optionally tellurium to produce a used mixed metal oxide catalyst; and
   contacting a gas stream comprising methane with the used mixed metal oxide catalyst at a temperature from 200 to 500° C. and at a pressure, wherein said gas stream comprises no or substantially no alkane containing 2 to 6 carbon atoms, no or substantially no alkene containing 2 to 6 carbon atoms, and no or substantially no oxygen.

2. The process according to claim 1, wherein the temperature is from 250 to 500 ° C.

3. The process according to claim 1, wherein the pressure is from 0.1 to 15 bara.

4. The process according to claim 1, wherein the gas stream further comprises an inert gas.

* * * * *